(12) United States Patent
Wester

(10) Patent No.: US 8,204,762 B2
(45) Date of Patent: *Jun. 19, 2012

(54) HEALTH CARE PATIENT BENEFITS ELIGIBILITY RESEARCH SYSTEM AND METHODS

(75) Inventor: John Wester, Austin, TX (US)

(73) Assignee: E-Scan Data Systems, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/857,350

(22) Filed: Aug. 16, 2010

(65) Prior Publication Data

US 2011/0301979 A1    Dec. 8, 2011

Related U.S. Application Data

(63) Continuation of application No. 11/098,295, filed on Apr. 4, 2005, now Pat. No. 7,778,850.

(60) Provisional application No. 60/654,028, filed on Feb. 17, 2005.

(51) Int. Cl.
  *G06Q 10/00* (2012.01)
  *G06Q 50/00* (2012.01)
  *G06Q 40/00* (2012.01)

(52) U.S. Cl. ........................ 705/2; 705/3; 705/4

(58) Field of Classification Search ............. 705/2–4
  See application file for complete search history.

(56) References Cited

U.S. PATENT DOCUMENTS

| | | | |
|---|---|---|---|
| 5,388,259 A | 2/1995 | Fleischman et al. | |
| 5,668,987 A | 9/1997 | Schneider | |
| 5,832,447 A | 11/1998 | Rieker et al. | |
| 5,835,897 A * | 11/1998 | Dang | 705/2 |
| 5,915,241 A * | 6/1999 | Giannini | 705/2 |
| 5,930,759 A | 7/1999 | Moore et al. | |
| 5,970,463 A | 10/1999 | Cave et al. | |
| 6,026,398 A | 2/2000 | Brown et al. | |
| 6,061,657 A * | 5/2000 | Whiting-O'Keefe | 705/2 |
| 6,067,523 A | 5/2000 | Bair et al. | |
| 6,108,665 A | 8/2000 | Bair et al. | |
| 6,112,298 A | 8/2000 | Deao et al. | |
| 6,139,494 A * | 10/2000 | Cairnes | 600/300 |
| 6,324,516 B1 | 11/2001 | Shults et al. | |
| 6,523,019 B1 | 2/2003 | Borthwick | |
| 6,728,697 B2 | 4/2004 | Leathers | |

(Continued)

OTHER PUBLICATIONS

Sandquist, Fred C., et al., "Integrating Heterogenous Computer Systems into a Hospital Information System", Proceedings of the Hawaii International Conference on System Science, 1983, p. 54-57.*

(Continued)

*Primary Examiner* — Jason Dunham
*Assistant Examiner* — Amber Altschul
(74) *Attorney, Agent, or Firm* — Cox Smith Matthews Incorporated

(57) ABSTRACT

The software of the present invention provides a means for creating a file of unpaid claims for a service provider. The software is used to create one or more queries to compare information in the file of claims against records in a benefit provider's database to determine the eligibility status of the claim. A file is created containing each claim for which a matching record in the benefit provider's database is found, and the information from that matching record. A report can be generated from the file of matching claims and benefit provider records, so the claims can be submitted for payment by the service provider.

36 Claims, 5 Drawing Sheets

U.S. PATENT DOCUMENTS

| | | | |
|---|---|---|---|
| 6,874,085 B1 * | 3/2005 | Koo et al. | 713/165 |
| 6,922,638 B1 | 7/2005 | Wallace et al. | |
| 7,478,081 B2 | 1/2009 | Hacigumus et al. | |
| 2002/0013906 A1 | 1/2002 | Wallach et al. | |
| 2002/0026328 A1 | 2/2002 | Westerkamp et al. | |
| 2002/0091552 A1 | 7/2002 | Dombroski | |
| 2002/0133503 A1 | 9/2002 | Amar et al. | |
| 2002/0169955 A1 | 11/2002 | Bryant, Jr. et al. | |
| 2002/0194166 A1 | 12/2002 | Fowler | |
| 2002/0196141 A1 | 12/2002 | Boone et al. | |
| 2003/0120632 A1 | 6/2003 | Casey et al. | |
| 2003/0171953 A1 | 9/2003 | Narayanan et al. | |
| 2003/0200118 A1 | 10/2003 | Lee et al. | |
| 2004/0073456 A1 | 4/2004 | Gottlieb et al. | |
| 2004/0078750 A1 | 4/2004 | Frank | |
| 2004/0111291 A1 | 6/2004 | Dust et al. | |
| 2004/0128165 A1 | 7/2004 | Block et al. | |
| 2004/0148203 A1 | 7/2004 | Whitaker et al. | |
| 2004/0172297 A1 | 9/2004 | Rao et al. | |
| 2004/0172313 A1 | 9/2004 | Stein et al. | |
| 2004/0243545 A1 | 12/2004 | Boone et al. | |
| 2005/0033609 A1 | 2/2005 | Yang | |
| 2005/0060185 A1 | 3/2005 | Balogh | |
| 2005/0084152 A1 | 4/2005 | McPeake et al. | |
| 2005/0154686 A1 | 7/2005 | Corston et al. | |
| 2005/0251429 A1 | 11/2005 | Ammer et al. | |
| 2005/0288972 A1 | 12/2005 | Marvin et al. | |
| 2006/0026156 A1 | 2/2006 | Zuleba | |
| 2006/0041487 A1 | 2/2006 | Santalo et al. | |
| 2006/0053093 A1 | 3/2006 | Bonham et al. | |

OTHER PUBLICATIONS

270/271 Health Care Eligibility Benefit Inquiry and Response, ValueOptions, Version 1.0. Jul. 3, 2003 (42 pages).
Hobson, "Clarification of the Health Information Portability and Accountability Act," House of Representatives, Oct. 22, 1997 (1 page).
H.R. 3323, "Administrative Simplification Compliance Act." Jan. 3, 2001 (6 pages).
The Rule Making Process for Administrative Simplification: What is Taking so Long? (no date) (2 pages).
HIPAA Administrative Simplification Compliance Deadlines (no date) (1 page).
45 CFR 160 & 162, "Health Insurance Reform: Standards for Electronic Transactions; Announcements of Designated Standard Maintenance Organizations" Aug. 17, 2000 (62 pages).
104th Congress, Public Law 104-191, "Health Insurance Portability and Accountability Act of 1996," (18 pages).
http://www.cms,hhs.gov/hipaageninfo/, General Information, web page accessed Jan. 23, 2008 (2 pages).
http://www.cms.hhs.gov/MMIS/03_MedicaidHIPAASim.asp, "Medicaid HIPAA Administrative Simplifications," webpage accessed Jan. 23, 2008 (2 pages).
http://www.cms.hhs.gov/TransactionCodeSets Stands/, "Transaction and Code Sets Standards," webpage accessed Jan. 23, 2008 (2 pages).
http://www.wedi.org/, "Workgroup for Electronic Data Interchange," webpage accessed Jan. 23, 2008 (2 pages).
http://www.medscape.com. HIPAA's Inner Workings: Data Standards Could Help You, Manisses Communications Group, Inc., 2001 (3 pages).
Health Care Eligibility Benefit Inquiry and Response, Washington Publishing Company, 2000, pp. 1-100 (100 pages).
Health Care Eligibility Benefit Inquiry and Response, Washington Publishing Company, 2000, pp. 101-200 (100 pages).
Health Care Eligibility Benefit Inquiry and Response, Washington Publishing Company, 2000, pp. 201-250 (50 pages).
Health Care Eligibility Benefit Inquiry and Response, Washington Publishing Company, 2000, pp. 251-300 (50 pages).
Health Care Eligibility Benefit Inquiry and Response, Washington Publishing Company, 2000, pp. 301-374 (74 pages).
Health Care Eligibility Benefit Inquiry and Response, Washington Publishing Company, 2000, pp. A1-E12 (70 pages).
Office Action dated Oct. 5, 2009 in U.S. Appl. No. 11/676,199 (8 pages).
Office Action dated Feb. 20, 2009 in U.S. Appl. No. 11/098,295 (9 pages).
Office Action dated Jul. 30, 2009 in U.S. Appl. No. 11/098,295 (11 pages).
Office Action dated Dec. 23, 2009 in U.S. Appl. No. 11/782,555 (14 pages).
Office Action dated Aug. 31, 2010 in U.S. Appl. No. 11/782,555 (16 pages).
Final rejection dated Jan. 4, 2012, issued in co-pending U.S. Appl. No. 11/782,555 (13 pages).
Final Rejection dated Oct. 18, 2011, issued in co-pending U.S. Appl. No. 12/880,978 (14 pages).
Response to Office Action filed on Jan. 17, 2012 in co-pending U.S. Appl. No. 12/880,978 (11 pages).

* cited by examiner

Figure 2A
Billable Report

| Sys Code Acct # Service Type | Patient Last, First, Middle Name Patient ID, D.O.B. | Total Charges Current Bal Eligible Amount | Service Date | Elig Start | Insured ID | Billing Deadline |
|---|---|---|---|---|---|---|
| | *(incorrect information shown on report, when different)* | | | | | |
| BILLABLE | | | | | | |
| HQST03249324 AMT30456 | Ruez, Juan 123456789  06/09/1965 *Ruiz, Juan* | 17,799.38 17,799.38 17,799.38 | 05/07/2004 | 11/12/2003 | 50494038 | 08/10/2005 |
| HQST03293240 FLTM3203 | Escobar, Latisha S 23456789  09/14/1983 *Escobar, Latishas* | 2,198.00 2,000.00 2,000.00 | 06/13/2003 | 12/10/2001 | 090324924 | 05/30/2005 |
| HQST3403240 FLDL5673 | Johnson, Charles Sr 345678975 *Johnsonsr, Charles* | 5,507.15 5,507.15 5,507.15 | 08/24/2003 | 08/10/2000 | 034034908 | 06/15/2005 |
| HQST3403240 FLDL5673 | Smith, John 345674455 | 2,300.65 2,300.65 2,300.65 | 03/24/2004 | 05/28/1995 | 034123456 | 07/15/2005 |
| *FID15678* | | | | | | |
| HQST039400 AMT04950 | Pitt, Bradley 987654321 | 1,785.74 1,000.00 850.00 | 03/08/2005 | 03/15/2005 | 340393402 | 06/08/2005 |
| *PAST BILL DEADLINE* | | | | | | |
| HQST03045945 CHK0568 | Espinosa, Norma 456789123 | 5,507.15 | 09/30/2003 | 10/30/2003 | 04950600 | 1/30/2004 |

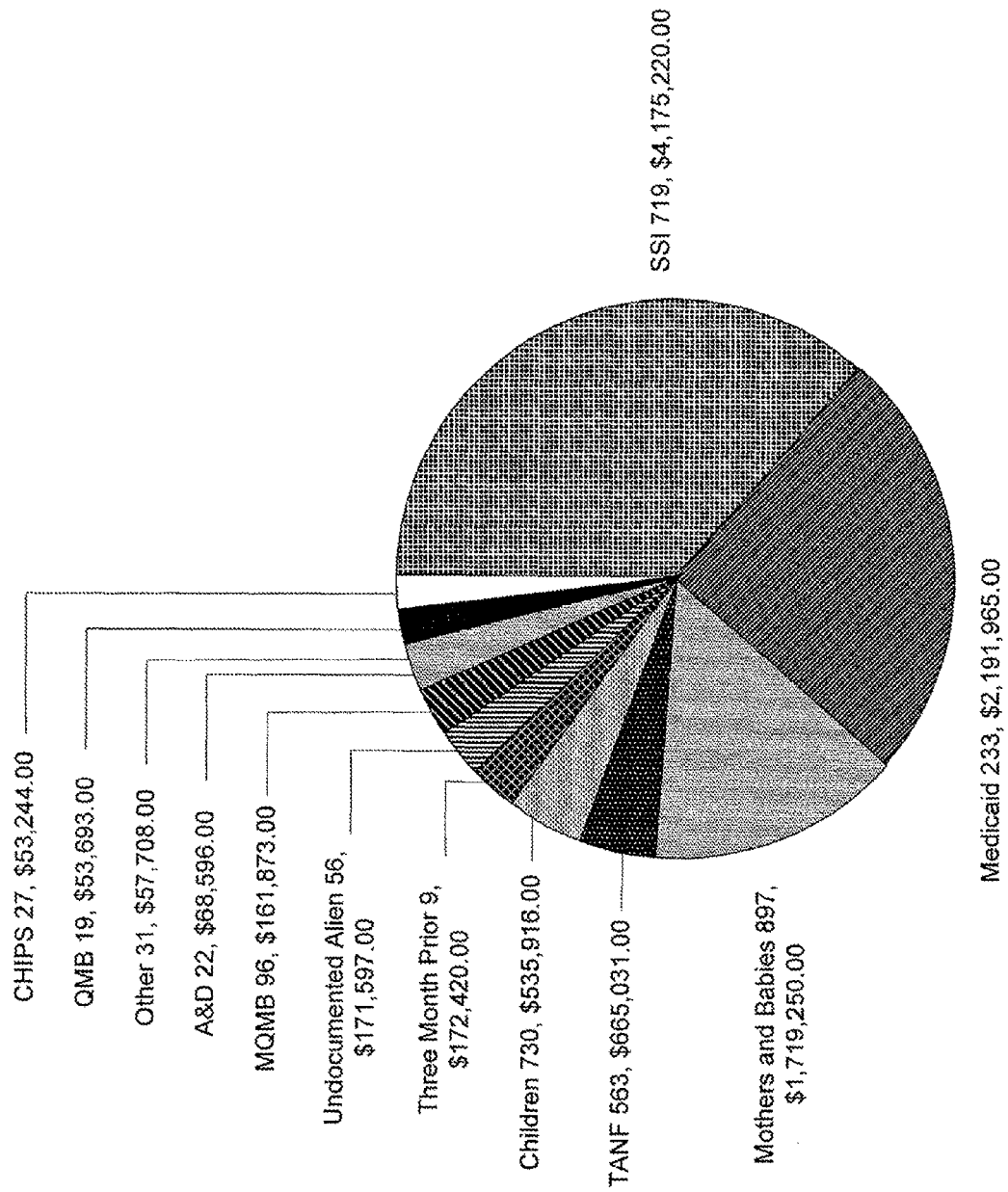

FIGURE 2C eScan Medicaid Recovery Report    May 2004 – Feb. 2005

| Hospital | Num Beds | May-04 | Jun-04 | Jul-04 | Aug-04 | Sep-04 | Oct-04 | Nov-04 | Dec-04 | Jan-05 | Feb-05 | Total |
|---|---|---|---|---|---|---|---|---|---|---|---|---|
| #1 | 349 | | $3,897 | $1,542 | $16,133 | $2,018 | $2,741 | $3,638 | $2,011 | $2,530 | | $34,490 |
| #2 | 1257 | $39,190 | $84,329 | $18,254 | $18,185 | $177,801 | $16,696 | $45,332 | $25,412 | $14,964 | $48,100 | $488,264 |
| #3 | 292 | $144 | $21,776 | $3,027 | $6,150 | $1,995 | $19,611 | $1,110 | $17,690 | $4,846 | $3,097 | $79,445 |
| #4 | 117 | | | | | | | | | | $24,601 | $24,601 |
| #5 | 385 | $2,959 | $2,839 | $3,969 | $11,769 | $2,047 | $31,040 | $7,851 | $13,474 | $11,797 | $16,028 | $103,774 |
| #6 | 167 | $3,709 | $7,112 | $3,414 | $7,046 | $2,632 | $1,636 | $11,387 | $12,011 | $11,532 | $1,664 | $62,145 |
| #7 | 73 | $28,295 | $6,903 | $7,015 | $11,323 | $2,861 | $3,145 | $15,338 | $17,260 | $14,346 | $1,449 | $107,934 |
| #8 | 84 | $659 | $4,851 | $2,335 | $2,143 | $2,785 | $6,921 | $1,130 | | $47 | $7,368 | $28,240 |
| #9 | 104 | $667 | $601 | $2,149 | $956 | $2,350 | $3,207 | $2,718 | $2,122 | $3,159 | $1,723 | $19,653 |
| #10 | 85 | $899 | $29 | $8,646 | $15,945 | $455 | $6,360 | $4,051 | $3,588 | $2,983 | $7,842 | $50,800 |
| #11 | 219 | $206 | $1,829 | $279 | $1,758 | $373 | $3,875 | $4,079 | $5,722 | $2,275 | $371 | $20,768 |
| #12 | 149 | $5,077 | | $25,389 | | $383 | | $373 | $21,493 | $15,506 | $17,746 | $85,966 |
| #13 | 67 | | | | | | | | $17,123 | $5,116 | $8,750 | $30,988 |
| #14 | 595 | $60,262 | $104,687 | $9,519 | $41,979 | $35,481 | $16,070 | $19,528 | $44,486 | $46,915 | $28,200 | $407,128 |
| #15 | 212 | $1,614 | $45,103 | $1,887 | $73,859 | $6,894 | $243 | $22,617 | $20,643 | $35,827 | $9,792 | $218,480 |
| #16 | 178 | | $6,263 | $6,139 | $3,457 | $717 | $255 | $7,982 | $13,872 | $5,824 | $3,919 | $48,426 |
| #17 | 858 | $130,305 | $71,164 | $161,036 | $104,048 | $226,591 | $18,945 | $182,213 | $228,168 | $47,576 | $122,693 | $1,292,738 |
| #18 | 65 | $2,486 | $12,943 | $1,200 | $1,931 | $13,285 | $442 | $1,510 | $5,707 | $586 | $10,133 | $50,222 |
| #19 | 80 | $979 | $3,271 | $2,249 | $1,624 | $4,348 | $657 | $3,857 | $709 | $6,295 | $2,113 | $26,100 |
| #20 | 344 | $58 | $1,843 | $17,127 | $2,012 | $2,302 | $3,390 | $7,843 | | $474 | $251 | $35,299 |
| #21 | 0 | | $2,545 | $3,988 | $12,586 | $6,151 | $2,650 | $9,823 | $2,491 | $5,534 | $6,124 | $51,892 |
| #22 | 256 | | $501 | $4,238 | $10,933 | $581 | $2,540 | $612 | | $16,056 | $9,219 | $44,681 |
| #23 | 536 | $98,224 | $26,781 | $24,222 | $48,337 | $39,604 | $20,892 | $36,229 | $29,458 | $19,539 | $9,660 | $352,946 |
| #24 | 103 | | $2,302 | | $1,302 | $1,055 | $161 | $2,054 | $485 | $683 | $896 | $8,937 |
| #25 | 321 | | | | | | | | | | $3,072 | $3,072 |
| #26 | 138 | | | | | | $8554 | $2,202 | $8,108 | $20,080 | $8,476 | $47,421 |
| #27 | 363 | $17,941 | $25,172 | $20,918 | $22,733 | $12,639 | $34,805 | $8,574 | $47,092 | $21,355 | $10,151 | $221,379 |
| #28 | 180 | $3,597 | $2,096 | $9,928 | $4,729 | $18,586 | $32,594 | $24,746 | $11,906 | $5,844 | $3,453 | $117,478 |
| #29 | 85 | $9,870 | $3,841 | $2,677 | $401 | $7,431 | | $4,660 | $1,127 | $528 | $2,062 | $32,596 |
| #30 | 542 | $22,508 | $9,427 | $11,414 | $28,978 | $8,133 | $66,281 | $13,260 | $55,099 | $19,255 | $37,719 | $272,071 |
| #31 | 360 | | | $27,397 | $41,849 | $33,641 | $68,619 | $35,540 | $28,627 | $67,561 | $13,089 | $316,303 |
| #32 | 407 | $21,170 | $14,956 | $8,314 | $1,530 | $13,763 | $31,804 | $2,332 | $23,843 | $29,908 | $28,979 | $176,599 |
| #33 | 21 | $7,530 | | $1,574 | $2,618 | | | $5,458 | $3,450 | $908 | $3,455 | $24,992 |
| Total | | $458,347 | $467,061 | $389,845 | $496,295 | $626,902 | $404,134 | $488,046 | $663,176 | $439,850 | $452,174 | $4,885,828 |

HEALTH CARE PATIENT BENEFITS ELIGIBILITY RESEARCH SYSTEM AND METHODS

CLAIM OF PRIORITY

This application is a continuation of U.S. patent application Ser. No. 11/098,295 filed Apr. 4, 2005 now U.S. Pat. No. 7,778,850, the disclosure of which is incorporated herein by reference, and claims priority from U.S. Provisional Patent Application No. 60/654,028 entitled "Health Care Patient Benefits Eligibility Research System and Business Method" filed on behalf of John Wester, on Feb. 17, 2005, the disclosure of which is incorporated herein by reference.

TECHNICAL FIELD

The invention relates generally to data processing software for inquiring and determining eligibility for reimbursement for patients by comparing the patient information against a benefit provider's database of covered persons to determine if the patient is eligible for benefits and, if so, associating the patient record with the matching record in the benefit provider's database so the service provider can seek to be reimbursed for the services provided to the patient.

BACKGROUND

The provision of health care services in the United States has become the focus of much attention. With the costs of medical malpractice insurance spiraling, and the payments being made to health care providers from benefit providers, including private and government insurers being reduced continually, health care providers are finding it necessary to get payments for all the services they actually render.

Unfortunately, many health care providers are not receiving compensation for the services they render. This could be due to a number of factors, such as patients not having the ability to pay for the services, and/or not having any medical payment system or insurance. In other instances, medical care service providers submit a request to determine if a patient is eligible for coverage under a private or government insurance plan, but are told the patient is not eligible for coverage. Often, payment for services rendered is denied due to incorrect data entry about a patient and/or the service rendered, through failure to associate the information with the correct patient record in the benefit provider's database, or other misunderstandings or mis-associations.

For medical care service providers, being denied payment for services rendered is problematic, and can, in some cases, mean the difference between profitability and a business that does not show a profit. Typically, such claims which are classified as not eligible for reimbursement are written off as bad debt for which collection cannot be achieved. Ultimately, these costs are either passed along to other patients by means of cost increases, or the care provided is cut back to save or reduce costs.

Accordingly, a continuing search has been directed to the development of methods which can help medical care service providers maximize identification of patients who are eligible for private or government medical insurance so the service providers can be reimbursed for claims.

Therefore, what is needed is a system and/or method for helping to efficiently identify claims for which the patients are eligible for health care benefits, which can be paid to the health care provider.

SUMMARY

Normally, claims for medical care are submitted to a patient's benefit provider for payment. Prior to submitting the claim, the health care provider will need to make an eligibility inquiry to determine whether the person for whom the service was provided is eligible for benefits; if not, payment to the health care provider will be denied. In many cases, the denial is because the information entered on the claim submitted to the benefit provider by the service provider cannot be correlated with the information in the benefit provider's database because the patient could not be located in the benefit provider's database due to inconsistencies. In some instances, this is due to a data entry error on the part of the service provider, benefit provider, or both. In other instances, the patient may not be eligible for insurance coverage at the time the services are rendered, or when the eligibility verification inquiry is made.

While software already exists that will make an eligibility inquiry to determine eligibility, and inquire as to correlation between records, there has been only partial success with automated eligibility verification inquiries. The existing software has only limited functionality and is not always effective or accurate. It will typically only search for records in which the patient's name, social security number and date of birth match a record in the benefit provider's database, and returns a list indicating only those patients for which an exact match has been found. It will not provide information as to numerous other issues that are related to eligibility, such as whether the service rendered is one paid for by the benefit provider. Additionally, manual examination is typically not practical or cost-effective, given the volume of patient claims and records.

The present invention provides a software program that will automatically, upon request, query benefit provider databases with a variety of different queries to find persons who are eligible to receive benefits, and who match patients in a service provider's database for whom services have been or may be provided. The software of the present invention will also automatically segregate those records for which there is a match between the databases for further processing, and can indicate the matching information found in the benefit provider's database. For example, the software of the present invention can inquire whether the patient is covered by the benefit plan, whether the services provided are covered by the benefit plan, and/or whether the provider is authorized to provide services for persons covered by that benefit plan.

The software of the present invention also provides means for comparing records in the benefit provider's database against a service provider's claims and finding records that, while not a complete match, have a predefined number of parameters that match, such that upon further analysis and correction, it may be determined that a patient claim is eligible for reimbursement and can be submitted to the benefit provider, and the service provider will be reimbursed for the services performed. The software of the present invention can easily reveal the field or fields in which there is a difference in the information between the service provider's claim and the benefit provider's database, making correction of any claim errors much simpler and making the present invention much more cost-effective than prior art which did not reveal any such partial matches, or show errors that had caused a claim that was submitted to have been rejected, but only verified whether or not there was a complete match.

The software of the present invention can also show whether the patient was qualified to be covered by a benefit plan at the time the services were rendered. In some instances, the patient was not eligible for coverage at the time the initial inquiry was made, but becomes eligible for coverage at a later time, and the coverage is retroactive back to a period including the time at which the service provider rendered treatment. If this retroactive eligibility is discovered and identified in a timely manner, a request for retroactive reimbursement can be made in some cases.

In other cases, even if the eligibility qualification is not discovered in time to seek reimbursement, the un-reimbursed claims can be important for a health care service provider in determining if it is entitled to reimbursement under various government programs for treating uninsured persons, and to help the service provider keep accurate track of how much of such funding they might be entitled to.

The present invention can also be used to generate reports in a variety of configurations, as to record matches found, to assist in identifying errors, determining sources of errors, and taking steps to prevent similar future errors. A surprising number of matches between service provider claims and benefit provider databases of persons eligible for reimbursement were found using the software of the present invention that were not found using prior art software. Even when the software of the present invention is used to query the same benefit provider's database for the same health care provider's claims, matches are found that were not found when the same or similar queries were previously made. These matches have resulted in tens of millions of dollars of reimbursements for service providers that would have otherwise gone unpaid.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIGS. 2A, 2B, and 2C show samples of some of the types of reports that can be generated from the file containing service provider claims for which there is a matching record in the benefit provider's database.

DETAILED DESCRIPTION

Figure 1A:
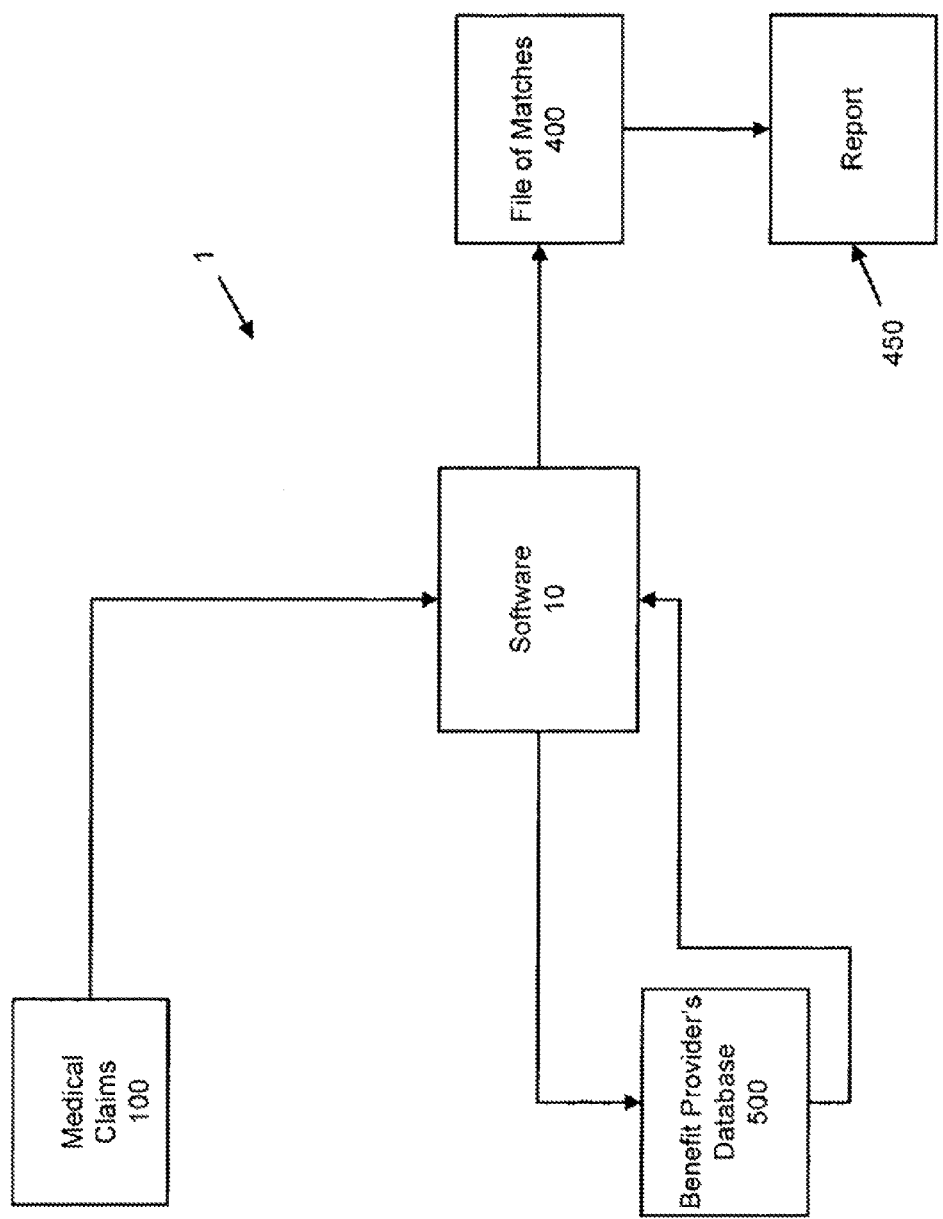
FIG. 1A is a high-level conceptual block diagram illustrating the system of the present invention.
Figure 1:
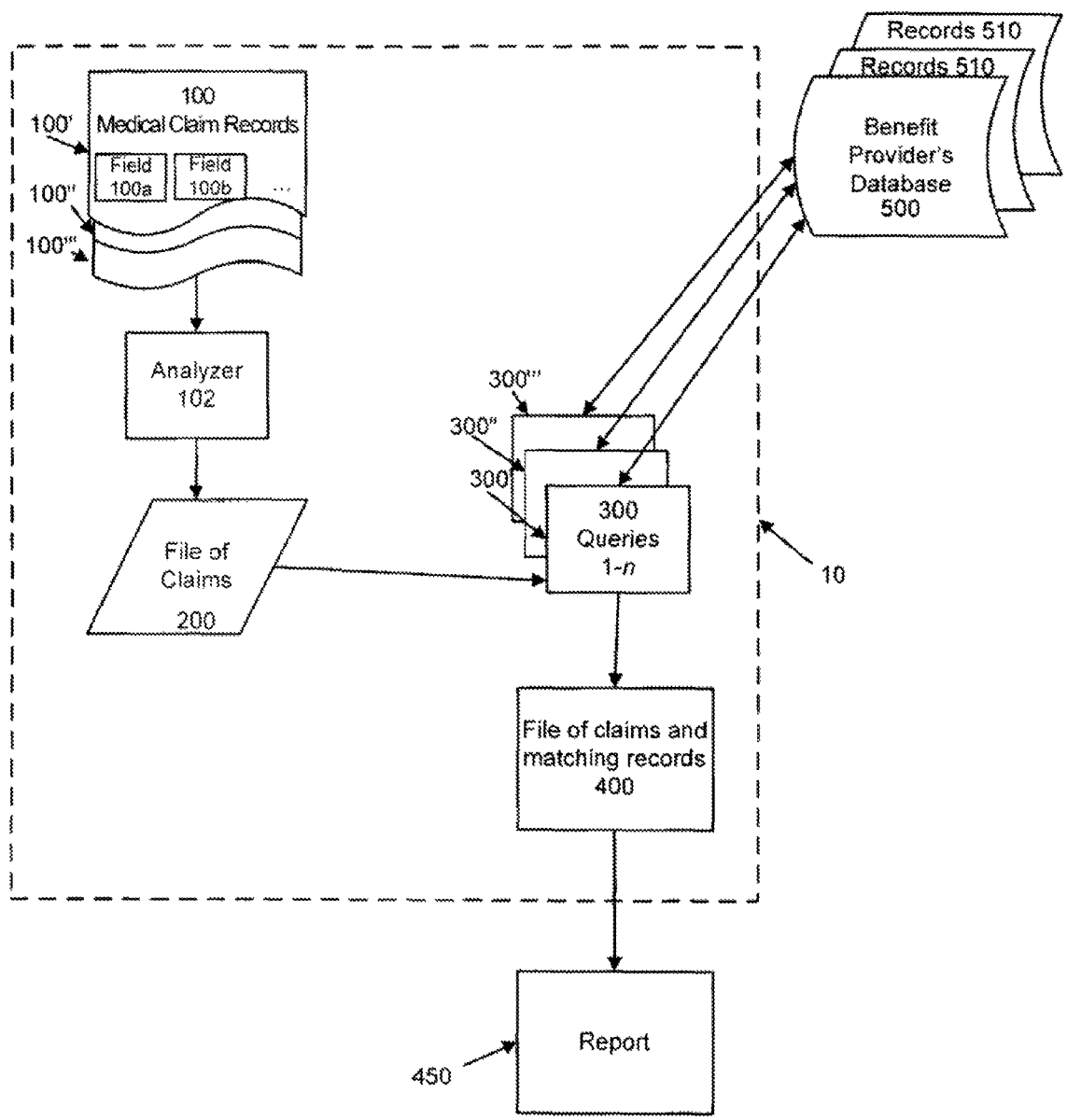
FIG. 1B is a detailed block diagram showing the querying of the benefit provider database, including comparison of service provider file records against the benefit provider's database, and generation of one or more files containing service provider's records and matching records from the benefit provider database.

In the discussion of the FIGURES, the same reference numerals will be used throughout to refer to the same or similar components. In the interest of conciseness, various other components known to the art, such as computer processing equipment, and the like necessary for the operation of the software, have not been shown or discussed.

In the following discussion, numerous specific details are set forth to provide a thorough understanding of the present invention. However, it will be obvious to those skilled in the art that the present invention may be practiced without such specific details. In other instances, well-known elements have been illustrated in schematic or block diagram form in order not to obscure the present invention in unnecessary detail. Additionally, for the most part, details concerning timing considerations and the like have been omitted inasmuch as such details are not considered necessary to obtain a complete understanding of the present invention, and are considered to be within the skills of persons of ordinary skill in the relevant art.

It is noted that, unless indicated otherwise, all functions described herein are performed by a processor such as a computer or electronic data processor in accordance with code such as computer program code, software, or integrated circuits that are coded to perform such functions. Additionally, it is noted that the software of the present invention can by used at a computer remote from the benefit provider's computer system and/or from the service provider's computer system, or locally to either of these computer systems.

A. Improved System

Referring to FIG. 1A of the drawings, the reference numeral 1 generally designates an improved eligibility verification inquiry system of the present invention. The inquiry system 1 comprises unpaid medical claims 100, software 10, benefit provider's database 500, files of matches 400, and reports 450 from the files of matches 400.

Normally, claims 100 for medical care are paid for by a patient directly, or submitted to a patient's benefit provider for payment, such as a private health insurance company, or government-subsidized health care insurance, such as Medicare, Medicaid or other government-funded programs. After processing to verify such things as whether the person for whom the service was provided is covered by the benefit provider, whether the services provided are covered by the benefit plan, whether the services were rendered during a period the patient was covered by the benefit provider, and whether the service provider is authorized to provide services for persons covered by that benefit plan, the benefit provider will pay the health care service provider for the service provided at a specified rate. However, if any of the numerous requirements are not met, the claim of the health care service provider is not submitted or processed for payment. When such a query for eligibility status is rejected, the health care service provider can seek to recover the fees due from the patient, or from a patient's secondary benefit provider, if any exists. Often, when all other recourse has been exhausted, the service provider must absorb the loss and not receive payment for the services provided.

Denial of eligibility for treatment is typically because the service provider is not authorized to provide service for persons covered by a specific benefit plan, the service provided is not covered by the benefit plan of the patient, the date on which the service was provided was not a covered date, or the patient is not covered by the benefit plan. In many cases, the denial is because the information entered on the claim submitted to the benefit provider by the service provider cannot be correlated with the information in the benefit provider's database, and therefore the claim is returned as ineligible. In reality, in many of these situations, the patient/service/date/ service provider are eligible claims within the scope of the benefit plan, but there is a mistake or difference in the information on the claim and the information in the benefit provider's database, and so the claim is not considered eligible for reimbursement.

Additionally, while in many cases, a claim 100 must be submitted within a certain time period after service is rendered, if the person becomes eligible retroactively, but after the allowed time period for filing claims, a request can be made for payment for services that were rendered that would be covered by the benefit plan. Thus, it is important to make inquiries as to eligibility status at frequent intervals to determine if a person is eligible while still within the time period during which a request for payment can be made.

Under certain new laws and regulations, such as the Health Insurance Privacy and Portability Act (HIPPA), which regulates the insurance benefit industry, service providers are authorized to access the benefit providers' databases 500, or to enable other parties to authorize the benefit providers' databases 500 on their behalf to make inquiries as to patient eligibility status. In some instances, if certain specifications are met as to the software used and other requirements, the benefit provider must make the information in their database available for such inquiries without charge. As an example, the software 10 of the present invention is fully compliant with the new laws and regulations.

B. Operation of the Present Invention

As shown in FIG. 1B, the software 10 of the present invention provides an analyzer 102 for converting and sorting a service provider's claims 100 and for generating a file of claims 200 in a form capable of being compared to the database of benefit providers 500 to find records 510 that match. The first step in the process encompassed by the software 10 is the generation of a file 200 containing the information from the service provider's unpaid claims 100 by the analyzer 102. Table 1 shows an example of the fields of a claim 100, although it should be appreciated that a variety of different numbers and arrangements of fields is possible. The exact fields 100a to 100n contained in each claim record 100 may vary, depending on what information is available in the service provider's records, and the information kept in the benefit provider's database 500.

TABLE 1

| Field | Example Claim Data |
| --- | --- |
| Patient ID No. | 12345678 |
| Patient Last Name | Smith |
| Patient First Name | John |
| Patient Middle Name | Q |
| Patient Date of Birth | Jan. 01, 2000 |
| Patient Address | 123 Main St. |
| Patient City | Anytown |
| Patient State | Texas |
| Patient Zip Code | 12345 |
| Patient Telephone No. | (214) 867-5309 |
| Benefit Plan Name | Medicaid |
| Benefit Plan No. | Type B |
| Insured's Name | Smith, John Q |
| Date of Service | Jan. 28, 2004 |
| Service Code | ABC1234 |
| Service Description | Emergency Room Visit |
| Charge Amount | 250.00 |
| Amount Paid | 000.00 |
| Balance Due | 250.00 |

Once the claim records 100 have been converted by the analyzer 102 to the proper format in file 200, the software 10 employs processing queries 300. These processing queries 300 utilize claim records 100 within file 200 as the basis of the collection of one or more queries 300', 300", and 300'", etc. of the benefit provider's database 500. Each claim record 100 in the file 200 will be in the same format so the information therein can be compared to the records 510 in the benefit provider's database 500. The file 200 will be saved by the software 10 in a format that can be read and compared to the fields in the benefit provider's database 500.

The queries 300 contain instructions for comparing the fields 100a to 100n in each claim 100 in the file 200 with the corresponding fields 510a to 510n in each record 510 in the benefit provider's database 500 of covered persons to determine if they contain matching information. Table 2 is an example of some of the types of queries 300 that can be executed using the software 10 of the present invention.

TABLE 2

| Name | Query Description |
| --- | --- |
| MC | Medicaid number only |
| SSN | Social Security number only |
| MC SSN | Medicaid & Social Security |
| MC DOB | Medicaid & Date of Birth |
| MC FNLN | Medicaid & First name, Last name |
| SSN DOB | Social Security & Date of Birth |
| SSN FNLN | Social Security & First name, Last name |
| SSN LNFNINV | SSN and First, Last Name switched |
| SSN LNMN | SSN & Last name, Middle name replacing First name |
| DOB FNLN G F | Date of Birth & First name, Last name & Gender (Female) |
| DOB FNLN G M | Date of Birth & First name, Last name & Gender (Male) |
| SSN LN | Social Security & Last name |
| SSN LNFNMIa | Social Security & full name, MI |
| SSN LNFNMIb | Social Security & last name, first name + MI |
| SSN LNFNMIc | Social Security & last name, first name + " " + MI |
| SSN LNFNMId | Social Security & last name + MI, first name |
| DOB FN4LN | DOB & first name, 1st 4 letters of last name |
| SSN 4LN | SSN & 1st 4 letters of last name |
| SSN LNFNMIe | Social Security & last name + MI, first name |
| DOB LNFNMIa | Date of Birth & full name, MI |
| DOB LNFNMIb | Date of Birth & last name, first name + MI |
| DOB LNFNMIc | Date of Birth & last name, first name + " " + MI |
| DOB LNFNMId | Date of Birth & last name + MI, first name |
| DOB LNFNMIe | Date of Birth & last name + " " + MI, first name |
| DOB LNFN | Date of Birth & last name, first name |
| DOB LNFNINV | Date of Birth & last name, first name switched |
| DOB LNMN | Date of Birth & last name, middle name replacing first name |
| DOB LNFNHA | DOB & first name, 1st half of hyphenated last name |
| DOB LNFNHB | DOB & first name, 2nd half of hyphenated last name |
| DOB LNFNHAB | DOB & first name, hyphen/space removed from last name |
| DOB LNFNHS | DOB & first name, hyphen -> space in last name |
| SSN LNFNHA | SSN & first name, 1st half of hyphenated last name |
| SSN LNFNHB | SSN & first name, 2nd half of hyphenated last name |
| SSN LNFNHAB | SSN & first name, hyphen/space removed from last name |
| SSN LNFNHS | SSN & first name, hyphen -> space in last name |

A query 300 can ask about a variety of information in various fields 510a-n in the records 510 in the benefit provider's database 500. For example, a query 300' could be as simple as checking to determine if the information in the patient identification number field 100a of a service provider's claim record 100' in the file 200 of claims matches the identification number field 510a in any records 510 in the benefit provider's database 500. Or, a query 300" could be more complex, and search for a variety of information matches, or partial matches, in multiple fields in the records 510 in the benefit provider's database 500. For example, the query 300" could check for claims 100 and records 510 in which both the date of birth fields 100b, 510b in the file 200 and benefit provider's database 500 match, and also the first 4 letters of the last name fields 100c, 510c match. It can be appreciated that a very large variety of queries 300 can be configured and used. The queries 300 can be virtually unlimited, as long as the information to be queried is available in the service provider's records 100 and in the benefit provider's database 500.

The software 10 of the present invention performs more queries 300, and more flexible queries of the benefit provider's database 500, and performs comparison and analysis to determine if there is a match between a claim 100 and record in the benefit provider's database 500, than the prior art software. In contrast, the prior art software made only limited queries, such as seeking to determine if the name, identification number and date of birth of the patient claim 100 matched a record 510 in the benefit provider's database 500.

It is this expanded scope and flexibility that results in the greater number of matched records than was found with prior art software. The software 10 of the present invention, in addition to finding matching records, because it does more queries 300, can also determine additional data about a claim 100, such as whether or not the claimed service is covered, the balance due on a claim 100, and even the amount of the balance due that is eligible for reimbursement. A surprising number of matches between service provider claims 100 and benefit provider databases 500 were found using the software of the present invention that were not found using prior art software. In one instance, a hospital, making just one set of queries 300, identified several million dollars in claims that were not previously found to be eligible for reimbursement.

Repeated execution of the queries 300 of the same benefit provider's database 500 at regular intervals, such as monthly or bi-weekly, continued to reveal claims 100 that were not eligible for reimbursement at the time the initial queries 300 were run, but subsequently became eligible for reimbursement. It can be appreciated that if these queries 300 were not subsequently run, the claims 100 found would not be reimbursed. Additionally, because there is typically a limited time period after a patient becomes eligible for benefits in which a claim 100 can be filed, it can be appreciated that if the queries 300 are not run at regular intervals, while matches could be found, they might be found too late for the service provider to seek reimbursement.

Additionally, it can be appreciated that identifying claims which would qualify for reimbursement under certain government medical programs would be important, even if reimbursement were not actually received, in order to help determine qualification for other government programs, and/or whether budget and funding estimates are accurate. For example, hospitals and other service providers that provide services to a large number of patients qualifying for Medicaid and/or Medicare could receive funding from another government fund for service providers who treat a disproportionate share of low-income patients. By using the results of the queries to identify qualifying patients, even if recovery cannot be made under the initial program, the treatment can be used for reporting and submitting requests for funding under secondary programs, such as the disproportionate share programs. For example, some patients who are treated who might qualify for reimbursement under state government managed programs may be from out of state, and therefore such a claim 100 may not be entitled to reimbursement. However, such unreimbursed claims may be used to qualify the service provider for reimbursement under secondary programs. The software 10 of the present invention can be used to provide reports as to the patients treated, anticipated and projected funding, whether the service provider is treating more or less low-income patients than projected, and potential entitlement for future programs. This information is very useful to a service provider, as knowing this information can be used to project budgets, deficits and qualification for additional funding.

Typically, the first query 300' might be to check for a person in the benefit provider's database 500 having a social security number/other unique identification number, and/or last name and first name that matches that of a patient for whom the hospital had provided services. Exactly which query 300 would be the first query 300' would depend on how the benefit provider structures its database records.

Additionally, a query 300 can also be a series of sequential queries. For example, a query 300' could be done to match the patient identification field 100a in a claim 100 with the patient identification field 510a for any matching record 510 from the benefit provider's database 500. If the patient ID number matches, then a second query 300" can be made between these matching records found in response to query 300' to determine if the date on which the service was provided falls within the dates of coverage provided by the benefit provider to that patient, and only if the answer to the second query 300" is also positive will the record be set aside in the file 400 for further processing. Alternatively, the system 10 could be configured so that if there is a match in the first electronic query 300', the records could be flagged and set aside, and the second query 300" could be done separately in a different query 300 or in or by a different system, or could even be done manually.

Note the software 10 can be configured so that all the queries 300 which are selected to be made could be run simultaneously or sequentially, or they could be grouped together and run sequentially. The purpose of different orders of queries or grouping of queries is to maximize efficiency of the software 10 of the present invention. The process in making such queries 300 of generally comparable records can also employ a variety of techniques, such as fuzzy and soundex searches. It should be appreciated that the queries 300 selected, the order in which they are performed, and the groupings of queries can be adapted or modified, depending on results returned from the queries 300.

Once the queries 300 to be run have been selected and generated by the software 10, the benefit provider's database 500 is accessed, and the software 10 of the present invention executes the first selected query 300' thereon. If one or more matching records 510' is found in the benefit provider's database 500 for a claim 100', the claim 100' is distinguished or flagged, removed from the file 200, and stored separately from the remainder of the claims 100 in the service provider's database 200 in a file 400, along with the information from matching records 510' from database 500. The purpose of removing the matched claim 100' from the file 200 is to streamline efficiency of the queries 300. Because one or more matches have already been made, there is no need to make additional queries 300 about this particular claim 100'. The query 300' will then be performed for the next claims 100" in the file 200 of service provider's claims, if any. If matches are found, then this claim 100" and the matching records 510" from the benefit provider's database 500 will also be stored in the file 400. If no match is found for claim 100", the claim remains in the file 200. Query 300' will be performed for each claim 100 in the file 200.

If, after making the initial query 300' of the benefit provider's database 500, there are still claims 100 in the service provider's file 200 that were not correlated with records 510 in the benefit provider's database 500, there are a variety of optional processes that could occur. No additional actions could be taken, and the claims 100 remaining in the file 200 would remain as ineligible status.

Alternatively, if there are additional queries 300", 300''', etc., that are in the selection of queries 300 to be made, the next query 300" can be made of the benefit provider's database 500 to try and find additional matches with claims 100 in the service provider's claims file 200. Again, for each claim 100 in the file 200, query 300" will be made of the benefit provider's database 500, and if any matches is found, that claim 100''' is flagged, placed in the file 400 and removed from the file 200 of unmatched claims. The software 10 then continues to make the same query 300" for each remaining claim 100 in the service provider's file 200. This cycle of querying/record flagging will continue until all claims 100 in the service provider's claims file 200 have been matched to at least a record 510 in the benefit provider's database 500, or until all queries specified have been made of the benefit provider's database 500 for all claims 100 in the service provider's claims file 200.

Once all the queries 300 of the benefit provider's database 500 have been run, the file 400 of all matched records is generated. In the file 400, each claim 100 is associated with the related matching record 510 from the benefit provider's database 500. For example, claim 100', from the file 200 which was associated with a record 510' from the benefit provider's database 500 will be grouped together in the file 400. The file 400 can be saved on a computer, or delivered via other methods, such as via the internet, as an attachment to an e-mail, as a facsimile, or as a physical document. A report 450 of contents of the file 400 can be generated and provided to the service provider so that the eligible claims can be submitted for payment by the service provider.

The report 450 can be delivered to the service provider in a variety of methods, depending on their preference, including delivery by e-mail, in paper form, or by internet or a variety of other forms. Reports 450 can include a variety of information such as the information from each claim 100 in the service provider's database for which any matching record 510 in the benefit provider's database 500 was found. FIGS. 2A, 2B, and 2C show samples of some of the many reports that can be generated using the software of the present invention.

As can be seen in the report in FIG. 2A, a listing is provided of claims for which a match was found in the benefit provider's database. Any information in the service provider's database that was incorrect or differed from that in the benefit provider's database is shown in different print for assistance in easily identifying the problem so the claim can be corrected.

As can be seen, the report 450 shown in FIG. 2A is organized so that the service provider can easily review the information to determine those records having errors, and exactly what the errors are, so the claims can be corrected and resubmitted. In contrast, the prior art software generated reports that simply listed names and identification numbers of patients for which a match was found in the benefit provider's database 500. No sorting of records was done as in the reports of the present invention, and no additional information was provided from the benefit provider's database 500, such as eligibility dates and billing deadlines, so additional manual analysis was required to determine if a claim could be submitted for payment. Additionally, because the prior art software did not do any multi-field comparisons or partial matches with analysis, records such as the first three shown in the sample report in FIG. 2A would not have been discovered at all.

A record such as the fourth record shown in the sample report in FIG. 2A, which would have appeared as eligible for reimbursement using software of the prior art, which only checked for a match of identifying information for the patient, would have resulted in a claim that was submitted being rejected, because the service type code was entered incorrectly. Using the software 10 of the present invention, which checks to see if the service rendered is eligible for reimbursement, would find the incorrect service code, which could be corrected before the claim 100 was submitted for reimbursement.

The fifth record shown in the sample report in FIG. 2A shows a claim 100 for which partial payment has been received, but for which there is still an outstanding balance. The software of the present invention has performed analysis to determine that the patient is covered by the benefit provider, and that the service is eligible for reimbursement. Therefore, the service provider can submit the claim 100 to seek to recover the outstanding balance. The report also shows the amount of the outstanding balance that is eligible for reimbursement. In this case, it is less than the full amount because the deductible for the benefit provider has not yet been met by this patient. This claim is also an example of a claim which has become eligible for benefits since the last time a report was run, and lists the date by which any claim must be made.

The last entry on the sample report of FIG. 2A shows a claim 100 that would have been qualified for reimbursement, had it been found and submitted in a timely manner. Such results would occur if the queries 300 of the present invention were not made on a regular basis.

FIG. 2B shows a pie chart break-out of an example of one instance in which the software 10 of the present invention was used showing the amount of claims eligible for reimbursement for a benefit provider, broken out by class of benefit provider the number of claims for each class, and the amount of money for the claims for each class. Additional information from the service provider's and benefit provider's records that would be useful to the service provider in submitting the claim is also provided, such as the deadline, if any, by which the claim must be submitted.

FIG. 2C shows a report that provides information about claim eligibility verification for a variety of service providers, including the amounts identified for the claims, broken out for queries made on a regular basis. As can be seen, while the number for subsequent queries 300 typically decreases, it can be seen that additional eligible claims are identified when the software 10 is used to make subsequent queries 300.

It should be appreciated that a variety of different reports, report formats, and information can be used, depending on the needs of the service provider. The information in the reports 450 can be used for a variety of functions, such as to track errors, and possibly reduce similar future errors made when submitting claims. Additionally, the reports 450 can be used to monitor query results to determine the effectiveness of a particular query 300. If a particular query 300 does not ever produce any record matches, a decision could be made to not continue to make that query 300, or to enhance it in some way so as to increase the likelihood of obtaining a match.

Depending on the benefit provider's system, claims for which a match was found can be filed on-line, and/or a manual submission of claims for which payment is requested can be made.

The software 10 can be modified continually or periodically to ensure compliance with various local, state and/or federal laws, depending on where it is used. Additionally, because the world of medical service and benefit providers is rapidly and continuously changing and evolving, the software 10 of the present invention has been designed to be flexible and adapt to ongoing changes in the industry.

C. Examples

It is appreciated that some examples may be helpful in illustrating the features of the present invention. If a service provider, such as a hospital, had a large number of claims 100 for services it had provided to patients (i.e. an emergency room visit, a hospital stay, etc.), the software 10 of the present invention could be used to inquire as to the status of the claims 100. The software 10 would first be used to generate a file 200 in the appropriate form that contained information for each claim 100. For purposes of this example, assume that there are 90 (ninety) claims 100 in the file 200.

The software 10 would also be used to develop a series of one or more queries 300 that could be made of the benefit provider's database of members to find members of the benefit provider's plan for whom the service provider had rendered service, but has not yet been reimbursed. Again, only for purposes of this example, assume that there are 2 queries to be made against the benefit provider database 500, sequentially, and a third query to be made for all records which were entered in file 400.

Typically, the first query 300' might be to check for a person in the benefit provider's database 500 having a social security number/other unique identification number, and/or last name and first name that matches that of a patient for whom the hospital had provided services. Exactly which query 300 would be the first query 300' would depend on how the benefit provider structures its database records.

Such an initial standard query is useful to patients eligible for reimbursement. In some situations, there is a delay in a patient being entered into a benefit provider's database, so if the claim is submitted to the benefit provider for payment before the patient has been added to the database, the claim 100 status will be returned as ineligible. Additionally, for some medical benefit programs, such as Medicaid and the Consolidated Omnibus Budget Reconciliation Act (COBRA), coverage can be retroactive. Similarly, in these situations, the patient may not appear in the database of persons qualifying for benefits under that plan when the patient is treated, or the database may indicate that the patient was not covered on the date the service was rendered. However, if the patient is added to the benefit provider's database subsequently, the claim will only be shown as "eligible" if the claim is re-submitted after the patient is in the benefit provider's database 500. In some instances, it has been found that several years can elapse before a claim 100 becomes eligible for reimbursement. However, in many cases, there is only a limited time allowed after a patient becomes eligible that claims 100 can be submitted to the benefit provider. Thus, queries 300 of the benefit provider's database 500 must be made on a regular basis so that eligible claims 100 can be identified in a timely manner, while the claim 100 can still be filed.

Another example of situations in which the patient may not appear in the benefit provider's database 500 when a claim is first submitted is for newborn babies. Such patients do not always have a unique ID number, such as a social security number, at birth. In some cases, there is even a delay in the patient being given a name, and the hospital records may simply refer to the child as "Baby Boy Smith." Thus, the hospital may not have the proper information available to it to be able to generate a claim with information that matches the benefit provider's database 500. Even if the hospital had the correct name or identifying information, these patients are not added to the insurer's database until after the child is born, and there is typically a delay in such information getting entered into the database. Thus, the hospital could submit a claim 100 immediately after the child is born, and there could be no related record 510 in the benefit provider's database 500 at that time. Thus, these claims 100 are often not paid because they cannot be matched up with a patient in the benefit provider's database 500. Again, making eligibility inquiries of the benefit provider's database on a regular basis will reveal that the patient has been added to the database 500 and the claim 100 is eligible for reimbursement.

Another example of claims 100 that this query 300' might find a match for would be an instance where the benefit provider matches records by patient name, rather than patient identification, and the benefit provider has a patient in its database 500 as John Smith, but the service provider submitted a claim for service provided to John Smithe. Because the benefit provider did not find John Smithe in its database, it originally rejected the claim as ineligible; however, because the patient IDs match, this query would make a match.

Once the queries 300 have been selected, the software 10 can be configured to run the selected queries 300 against the benefit provider's database 500 to find records that match any of the claims 100 in the file of the service provider's unpaid claims 200. Again, for purposes of this example, assume that the first query 300' is to find an exact match between the patient ID fields of any claim 100 in the file of the hospital's claims 200, and any patient record 510 in the benefit provider's database 500. Assume that when query 300' has been run, and the data in each of the ninety claims 100 in the service provider's file 200 has been compared to the records 510 in the benefit provider's database 500, twenty of the claims 100 are found to have matching records 510 in the benefit provider's database, therefore being eligible for reimbursement. When a match is found for a claim 100' in the benefit provider's database, that claim 100' and the information from the matching record 510' in the benefit provider's database 500 is placed in a file 400. Each claim 100 which has been matched to a record 510 from the benefit provider's database 500 is removed from the file 200 after query 300' has been run and completed. Thus, after the first query 300' has been run, only seventy claims 100 will remain in the file 200.

For purposes of this example, assume the second query 300" is a query to find claims 100 in the seventy remaining claims in the file 200 for which the date of birth field is the same as the date of birth field in a record 510 in the benefit provider's database 500, the first name fields are the same, and the first four letters of the last name field are the same. This query would find patients for whom the patient ID was entered incorrectly, but the name and date of birth information was correct. Thus, if for patient Thomas Jones, his ID number was incorrectly entered in the service provider's claim as 12345679, but the actual ID number was 12345678, the first query 300' would not find a matching record 510 in the benefit provider's database 500. However, the second query 300" would find a matching record 510.

After the first query 300' has been run, the second query 300" is run for the remaining seventy claims 100 in the file 200. Assume this query results in another twenty claims 100 being matched with one or more records 510 in the benefit provider's database 500. Each of these twenty claims is also removed from file 200 and placed in file 400, leaving only fifty claims 100 in the file 200. It can be appreciated that with queries 300" such as this, multiple matches could be found with persons having the same date of birth, first name, and last four digits of the last name, and therefore, multiple records 510 could be returned that potentially match a claim 100.

When all the queries 300 have been run, the software 10 will exit the query of the benefit provider's database 500, and a file 400 of all matched records is generated. In the case of this example, file 400 contains forty claims 100 for which one or more matches has been made in the benefit provider's database 500. The file 400 contains the information from each claim 100 for which a matching record 510 in the benefit provider's database 500 was found, and the information from the matching record(s) 510 in the benefit provider's database. A report 450 of contents of the file 400 can be generated and provided to the service provider so that the matched claims can be submitted to the benefit provider.

However, in the case of this example, the software runs a query 300''' on all forty records in the file 400 to determine if the date by which a claim must be submitted for reimbursement is later than the present date. If not, that claim could be flagged in the file 400 as being a past deadline claim. Or, it could be a query that would check for additional matching fields between claims 100 that have generated more than one matching record 510 from the benefit provider's database 500. It can be appreciated that this query could have been made as part of the first or second queries 300', 300'' of the benefit provider's database 500, or as a separate query 300 of the benefit provider's database 500. However, again, only for the purposes of this example, assume that it was found to be much more efficient to make this date query 300''' after file 400 had been generated, rather than as a query to the benefit provider's database 500. Additionally, such information about claims qualifying for payment could be important for tracking whether a health care service provider qualifies for reimbursement from other programs, such as disproportionate share Medicaid or Medicare reimbursement funds, as discussed above. If this query was performed before the claim 100 was placed in the file 400, the claim 100 might not be placed in the file 400, and therefore it could be difficult to track this type of information when preparing reports to determine qualification for the additional programs. Alternatively, it can be appreciated that further inquiries such as this could be made manually upon review of the report 450 of matching files 400. Again, how such analysis is performed depends on the specific needs of a user.

If appropriate, additional analysis can be made of the service provider's claims 100 and any matching records 510 from the benefit provider's database 500 to determine if there are additional fields that match between the record in the benefit provider's database and the claim to ensure the patient is the same entity. For example, if multiple records 510 are returned that same date of birth, first name, and first 4 digits of the last name, additional analysis can be done to look for additional matches in other fields, or determine the probability that a specific record 510 matches a specific claim 100'.

In one arrangement of the present invention, queries 300 can be run of the benefit provider's database 500, with charges being incurred on a per query basis, as per the prior art software. In another arrangement of the present invention, because the software 10 of the present invention complies with the requirements of the new laws governing such queries 300, the queries 300 can be run without charge for the number of queries run, or the number of times queries are run. If the queries 300 are made by a third party on behalf of the service provider, payment to the third party can be made based on the number of claims 100 that are matched to database records 510, and for which payment is received by the service provider.

It is understood that the present invention can take many forms and embodiments. Accordingly, several variations may be made in the foregoing without departing from the spirit or the scope of the invention. Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

The invention claimed is:

1. A tangible, non-transitory computer program product for comparing a service provider's medical care claims against a benefit provider's database, the computer program product having a computer readable medium with a computer program executable by a computer embodied thereon, the computer program comprising instructions which, when executed by the computer, cause the computer to perform the following operations:
  a. generating a first file of claims from the service provider, wherein said first file is organized such that data associated with at least two fields for each of the claims is formatted for comparison with the benefit provider's database, wherein the at least two fields are different from each other;
  b. executing a first query of the benefit provider's database using data from one of said at least two fields for a claim in the first file and executing a second query of the benefit provider's database using data from another of said at least two fields for said claim;
  c. adding said claim to a second file if a record in the benefit provider's database is responsive to said first query and said second query; and
  d. generating a report indicative of one or more differences between said claim for which a responsive record was found and said responsive record.

2. The tangible computer program product of claim 1 further comprising instructions for executing a first group of queries along with said first query wherein each query among the first group of queries uses data in at least one field from different claims in the first file in a comparison to data in corresponding fields in records in the benefit provider's database.

3. The tangible computer program product of claim 2 wherein the data used in each individual query among the first group of queries is related to a patient identification number and the corresponding fields in records in the benefit provider's database are related to a patient identification number.

4. The tangible computer program product of claim 2 further comprising instructions for tracking the effectiveness of queries.

5. The tangible computer program product of claim 4 wherein the effectiveness of queries is based on whether it produces one or more responsive records from the benefit provider's database.

6. The tangible computer program product of claim 4 further comprising instructions for adaptively modifying queries based on the effectiveness of queries.

7. The tangible computer program product of claim 6 wherein the modifying of queries is executed automatically.

8. The tangible computer program product of claim 1 wherein the data used in either of the first query or the second query is a subset of data associated with a field.

9. The tangible computer program product of claim 8 wherein the subset of data is the first four letters of an individual's last name.

10. The tangible computer program product of claim 1 wherein either the first query or the second query searches for partial matches of data in multiple different fields.

11. The tangible computer program product of claim 1 wherein said claim is added to the second file because the data in a predefined number of fields match with at least one record in said benefit provider's database.

12. The tangible computer program product of claim 1 wherein the first query and the second query are run sequentially.

13. The tangible computer program product of claim 1 wherein the first query and the second query are run simultaneously.

14. A tangible, non-transitory computer program product for comparing a service provider's medical care claims against a benefit provider's database, the computer program product having a computer readable medium with a computer program executable by a computer embodied thereon, the computer program comprising instructions which, when executed by the computer, cause the computer to perform the following operations:
   a. generating a first file comprising claims from the service provider formatted for comparison with the benefit provider's database;
   b. executing a first query of the benefit provider's database using data from a claim in the first file and adding the claim to a second file if one or more records in the benefit provider's database are responsive to said first query;
   c. establishing one or more time intervals and executing one or more additional queries of the benefit provider's database using data from said claim following the one or more time intervals if no record of the benefit provider's database is responsive to said first query; and
   d. adding said claim to said second file if one or more records in the benefit provider's database are responsive to said one or more additional queries, wherein the one or more responsive records in the benefit provider's database comprise new or corrected information following the one or more time intervals.

15. The computer program product of claim 14 wherein the one or more time intervals are related to a duration wherein a patient who was not found to be eligible for reimbursement before the one or more time intervals is found to be eligible for reimbursement after the one or more time intervals.

16. The computer program product of claim 14 wherein the one or more time intervals are bi-weekly or monthly.

17. The computer program product of claim 14 wherein at least one claim in said first file is related to a newborn baby.

18. The computer program product of claim 14 further comprising instructions for not re-executing a given query prior to the one or more time intervals if one or more records in the benefit provider's database are responsive to said given query upon an initial execution of said given query.

19. A tangible, non-transitory computer program product for comparing a service provider's medical care claims against a benefit provider's database, the computer program product having a computer readable medium with a computer program executable by a computer embodied thereon, the computer program comprising instructions which, when executed by the computer, cause the computer to perform the following operations:
   a. generating a first file comprising claims from the service provider, wherein said first file is organized such that data associated with at least one field for each of said claims in said first file is formatted for comparison with the benefit provider's database;
   b. executing a first query of the benefit provider's database, wherein the first query compares data in at least one field of a first claim in the first file with the benefit provider's database, and adding the first claim to a second file if one or more records in the benefit provider's database are responsive to said first query;
   c. executing a second query of the benefit provider's database, wherein the second query compares data in at least one field of a second claim in the first file with the benefit provider's database, and adding the second claim to the second file if one or more records in the benefit provider's database are responsive to said second query; and
   d. generating a report including data from claims in the second file and data from responsive records in the benefit provider's database, wherein differences between the claims from the second file and the responsive records from the benefit provider's database are shown.

20. The tangible computer program product of claim 19 further comprising:
   a. instructions for executing a first group of queries wherein each individual query in the first group of queries uses data associated with a different claim in the first file and compares that data to the same corresponding fields in records in the benefit provider's database as compared in said first query;
   b. instructions for adding a first subset of claims to a second file based on the results of the first query and the first group of queries;
   c. instructions for executing a second group of queries wherein each individual query in the second group of queries uses data associated with a different claim in the first file and compares that data to the same corresponding fields in records in the benefit provider's database as compared in said first query;
   wherein the second query and the second group of queries use data associated with claims in the first file that are not part of the first subset of claims.

21. The tangible computer program product of claim 19 further comprising instructions for executing a first group of queries along with said first query wherein each query among the first group of queries uses data in at least one field from different claims in the first file in a comparison to data in corresponding fields in records in the benefit provider's database.

22. The tangible computer program product of claim 21 wherein the data used in each individual query among the first group of queries is related to a patient identification number and the corresponding fields in records in the benefit provider's database are related to a patient identification number.

23. The tangible computer program product of claim 21 further comprising instructions for tracking the effectiveness of queries.

24. The tangible computer program product of claim 23 wherein the effectiveness of a query is based on whether such query produces one or more responsive records from the benefit provider's database.

25. The tangible computer program product of claim 23 further comprising instructions for adaptively modifying queries based on the effectiveness of queries.

26. The tangible computer program product of claim 25 wherein the modifying of queries is executed automatically.

27. The tangible computer program product of claim 19 wherein the data used in either of the first query or the second query is a subset of data associated with a field.

28. The tangible computer program product of claim 27 wherein the subset of data is the first four letters of an individual's last name.

29. The tangible computer program product of claim 19 wherein either the first query or the second query searches for partial matches of data in multiple different fields.

30. The tangible computer program product of claim 19 wherein at least one of said first claim and said second claim is added to the second file because the data in a predefined number of fields match with at least one record in said benefit provider's database.

31. The tangible computer program product of claim 19 wherein the first query and the second query are run sequentially.

32. The tangible computer program product of claim 19 wherein the first query and the second query are run simultaneously.

33. A tangible, non-transitory computer program product for comparing a service provider's medical care claims against a benefit provider's database, the computer program product having a computer readable medium with a computer program executable by a computer embodied thereon, the computer program comprising instructions which, when executed by the computer, cause the computer to perform the following operations:
   a. generating a first file comprising claims from the service provider, wherein said first file is organized such that data associated with at least two fields for each of said claims in said first file is formatted for comparison with the benefit provider's database;
   b. for each of said claims, executing a first query of the benefit provider's database, wherein the first query compares data in a first field of a respective claim in the first file with the benefit provider's database, and adding the respective claim to a second file if one or more records in the benefit provider's database are responsive to said first query;
   c. for each of said claims, executing a second query of the benefit provider's database if no records in the benefit provider's database are responsive to said first query, wherein the second query compares data in a second field of the respective claim in the first file with the benefit provider's database, and adding the respective claim to the second file if one or more records in the benefit provider's database are responsive to said second query; and
   d. generating a report including data from claims in the second file and data from responsive records in the benefit provider's database, wherein differences between the claims from the second file and the responsive records from the benefit provider's database are shown.

34. The tangible computer program product of claim 33 wherein said first field comprises a patient identification number and said second field comprises a name.

35. The tangible computer program product of claim 33 wherein the second query compares data in multiple fields other than the first field of the respective claim in the first file with the benefit provider's database.

36. The tangible computer program product of claim 35 wherein said first field comprises a patient identification number and wherein said multiple fields comprise a date of birth, a first name, and the first four letters of a last name.

\* \* \* \* \*